(12) United States Patent
Mueller

(10) Patent No.: US 9,028,478 B2
(45) Date of Patent: May 12, 2015

(54) ARTICULATING SURGICAL APPARATUS

(75) Inventor: Peter M. Mueller, Frederick, CO (US)

(73) Assignee: Covidien LP, Mansfield, MA (US)

( * ) Notice: Subject to any disclaimer, the term of this patent is extended or adjusted under 35 U.S.C. 154(b) by 965 days.

(21) Appl. No.: 13/186,654

(22) Filed: Jul. 20, 2011

(65) Prior Publication Data
US 2013/0023872 A1   Jan. 24, 2013

(51) Int. Cl.
| | | |
|---|---|---|
| *A61B 18/18* | (2006.01) | |
| *A61B 17/29* | (2006.01) | |
| *A61B 18/14* | (2006.01) | |
| *A61B 17/00* | (2006.01) | |
| *A61B 19/00* | (2006.01) | |

(52) U.S. Cl.
CPC ....... *A61B 17/29* (2013.01); *A61B 2017/00314* (2013.01); *A61B 2017/00327* (2013.01); *A61B 18/1445* (2013.01); *A61B 2019/266* (2013.01)

(58) Field of Classification Search
CPC ............... A61B 17/29; A61B 18/1445; A61B 2017/00314; A61B 2019/266; A61B 2017/00327
USPC ...................................................... 606/32–52
See application file for complete search history.

(56) References Cited

U.S. PATENT DOCUMENTS

| | | |
|---|---|---|
| 3,306,634 A | 2/1967 | Groves et al. |
| 5,374,277 A | 12/1994 | Hassler |
| 5,417,203 A | 5/1995 | Tovey et al. |
| 5,476,479 A | 12/1995 | Green et al. |
| 5,483,952 A | 1/1996 | Aranyi |
| 5,501,654 A | 3/1996 | Failla et al. |
| 5,601,572 A | 2/1997 | Middleman et al. |
| 5,609,601 A | 3/1997 | Kolesa et al. |
| 5,673,840 A | 10/1997 | Schulze et al. |
| 5,704,534 A | 1/1998 | Huitema et al. |
| 5,762,067 A | 6/1998 | Dunham et al. |
| 5,820,009 A | 10/1998 | Melling et al. |
| 5,823,066 A | 10/1998 | Huitema et al. |
| 5,860,995 A | 1/1999 | Berkelaar |
| 5,904,667 A | 5/1999 | Falwell |
| 6,063,098 A | 5/2000 | Houser et al. |
| 6,083,234 A | 7/2000 | Nicholas et al. |
| 7,533,906 B2 | 5/2009 | Luettgen et al. |
| 7,588,176 B2 | 9/2009 | Timm et al. |
| 7,588,546 B2 | 9/2009 | de Andrade |
| 7,588,575 B2 | 9/2009 | Colleran et al. |
| 7,608,081 B2 | 10/2009 | Abdelgany |
| 7,615,067 B2 | 11/2009 | Lee et al. |
| 7,618,442 B2 | 11/2009 | Spitler et al. |
| 7,637,410 B2 | 12/2009 | Marczyk |
| 7,670,334 B2 | 3/2010 | Hueil et al. |
| 7,789,283 B2 | 9/2010 | Shah |

(Continued)

*Primary Examiner* — Joseph Stoklosa
*Assistant Examiner* — Amanda Scott

(57) ABSTRACT

An endoscopic instrument includes a housing having shaft extending therefrom that defines a longitudinal axis therethrough. The shaft includes an articulating section disposed thereon. The articulating section has a central annulus extending therealong and first and second pluralities of bores. The first plurality of bores configured to receive corresponding tendons therethrough and the second plurality of bores configured to receive corresponding conductive leads therethrough. An end effector assembly operatively connected to a distal end of the shaft including a pair of first and second jaw members. The corresponding conductive leads transition from a first state for enabling articulation of the shaft about the articulating section, to a second state for disabling articulation of the shaft about the articulating section.

17 Claims, 3 Drawing Sheets

(56) References Cited

U.S. PATENT DOCUMENTS

| | | |
|---|---|---|
| 7,819,296 B2 | 10/2010 | Hueil et al. |
| 7,819,297 B2 | 10/2010 | Doll et al. |
| 7,819,298 B2 | 10/2010 | Hall et al. |
| 7,824,411 B2 | 11/2010 | Varieur et al. |
| 7,824,413 B2 | 11/2010 | Varieur et al. |
| 7,832,612 B2 | 11/2010 | Baxter, III et al. |
| 7,837,080 B2 | 11/2010 | Schwemberger |
| 7,842,044 B2 | 11/2010 | Runco et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,887,539 B2 | 2/2011 | Dunbar, Jr. et al. |
| 7,887,541 B2 | 2/2011 | Runco et al. |
| 7,905,380 B2 | 3/2011 | Shelton, IV et al. |
| 7,905,381 B2 | 3/2011 | Baxter, III et al. |
| 7,905,907 B2 | 3/2011 | Spitler et al. |
| 7,922,061 B2 | 4/2011 | Shelton, IV et al. |
| 7,931,677 B2 | 4/2011 | Abdelgany |
| 7,934,630 B2 | 5/2011 | Shelton, IV et al. |
| 2005/0149048 A1 | 7/2005 | Leport et al. |
| 2005/0240178 A1* | 10/2005 | Morley et al. ............. 606/51 |
| 2006/0178556 A1 | 8/2006 | Hasser et al. |
| 2007/0027468 A1 | 2/2007 | Wales et al. |
| 2007/0123855 A1* | 5/2007 | Morley et al. ............. 606/48 |
| 2007/0219550 A1 | 9/2007 | Thompson et al. |
| 2007/0221701 A1 | 9/2007 | Ortiz et al. |
| 2007/0225562 A1 | 9/2007 | Spivey et al. |
| 2008/0039776 A1 | 2/2008 | Ghabrial et al. |
| 2009/0023986 A1 | 1/2009 | Stewart et al. |
| 2009/0065549 A1 | 3/2009 | Viola |
| 2009/0088792 A1 | 4/2009 | Hoell, Jr. et al. |
| 2009/0125019 A1 | 5/2009 | Douglass et al. |
| 2009/0137984 A1 | 5/2009 | Minnelli |
| 2010/0030018 A1 | 2/2010 | Fortier et al. |
| 2010/0057121 A1 | 3/2010 | Piskun et al. |
| 2010/0076433 A1* | 3/2010 | Taylor et al. ............. 606/52 |
| 2010/0179540 A1 | 7/2010 | Marczyk et al. |
| 2010/0298638 A1 | 11/2010 | Slater |
| 2010/0298854 A1 | 11/2010 | Slater |

* cited by examiner

ARTICULATING SURGICAL APPARATUS

BACKGROUND

1. Technical Field

The present disclosure relates to an articulating surgical apparatus. More particularly, the present disclosure relates to an articulating surgical apparatus including an articulating section configured to lock the surgical apparatus in a non-articulated configuration.

2. Description of Related Art

Surgical instruments that are configured to articulate or bend are well known in the medical arts. Surgical instruments of this nature are utilized in many surgical procedures. For example, laparoscopic, endoscopic, or other minimally invasive surgical procedures are just a few of the many surgical procedures where articulating surgical instruments may find use. When utilized in such procedures, the surgical instruments may include a housing, a handle assembly, an articulating shaft, a device for articulating the shaft, and an end effector including a pair of jaw members.

As can be appreciated, the relatively small operable working space that is created within a cavity of a patient during a surgical procedure often makes it difficult for the surgeon to position the jaw members adjacent or close to target tissue. The articulating shaft allows a surgeon to position the jaw members adjacent target tissue.

Various articulating devices or mechanisms may be utilized to articulate the shaft. For example, some surgical instruments utilize one or more articulating cables or tendons that couple to one or more articulation links on the shaft. Typically, the cables or tendons provide a mechanical interface from the one or more articulation links to an actuation device, e.g., rotatable dials, disposed on the housing and/or handle assembly of the surgical instrument such that actuation of the actuation device moves or articulates the shaft about the articulation links. In particular, the cables or tendons are "pulled" or otherwise manipulated via one or more mechanisms in the handle assembly or the housing to articulate the shaft about the articulating links.

Under certain surgical scenarios, it may prove advantageous to maintain the shaft in a relatively fixed or stationary position, such as, for example, when positioning tissue between the jaw members or when the shaft is inserted through a trocar or cannula. Locking the cables or tendons so that the shaft is prevented from articulating typically requires eliminating, what is commonly referred to in the art as, cable or tendon "stretch" from the cables or tendons. Cable or tendon "stretch" is the ability of the cable or tendon to stretch under a predetermined load. To remove this cable or tendon stretch, the cables or tendons are typically highly loaded in tension. Removing this cable or tendon stretch limits and/or eliminates "post lock" articulation. However, due to the length of the surgical instrument and, thus, the corresponding length of the cables or tendons between the articulating links and the actuation device and/or locking device, a fairly large "spring rate" exists with a corresponding "stiffness" penalty being observed. That is, overtime, subjecting the cables or tendons to high load tension reduces the stiffness of the cables or tendons and, thus, the overall stiffness of the shaft. As can be appreciated, reducing the "stiffness" of the shaft may result in the shaft not functioning in a manner as intended.

SUMMARY

The present disclosure provides an endoscopic instrument. The endoscopic instrument includes a housing having shaft extending therefrom that defines a longitudinal axis therethrough. The shaft includes an articulating section disposed thereon. The articulating section has a central annulus extending therealong and first and second pluralities of bores. The first plurality of bores configured to receive corresponding tendons therethrough and the second plurality of bores configured to receive corresponding conductive leads therethrough. An end effector assembly operatively connected to a distal end of the shaft configured to treat tissue includes a pair of first and second jaw members. The corresponding conductive leads transition from a first state for enabling articulation of the shaft about the articulating section, to a second state for disabling articulation of the shaft about the articulating section.

The present disclosure provides an endoscopic instrument. The endoscopic instrument includes a housing having shaft extending therefrom that defines a longitudinal axis therethrough. The shaft includes an articulating section disposed thereon. The articulating section has a central annulus extending therealong and first and second pluralities of bores. The first plurality of bores configured to receive corresponding tendons therethrough and the second plurality of bores configured to receive corresponding conductive leads therethrough. An end effector assembly operatively connected to a distal end of the shaft includes a pair of first and second jaw members. One or both of the first and second jaw members being movable relative to other jaw member from an open position, wherein the first and second jaw members are disposed in spaced relation relative to one another, to a clamping position, wherein the first and second jaw members cooperate to grasp tissue therebetween. The corresponding conductive leads transition from a first state for enabling articulation of the shaft about the articulating section, to a second state for disabling articulation of the shaft about the articulating section.

The present disclosure provides a system for performing an electrosurgical procedure. The system includes an electrosurgical generator. The system includes an endoscopic instrument including a housing having shaft extending therefrom that defines a longitudinal axis therethrough. The shaft includes an articulating section disposed thereon. The articulating section has a central annulus extending therealong and first and second pluralities of bores. The first plurality of bores configured to receive corresponding tendons therethrough and the second plurality of bores configured to receive corresponding conductive leads therethrough. An end effector assembly operatively connected to a distal end of the shaft configured to treat tissue includes a pair of first and second jaw members. The corresponding conductive leads transition from a first state for enabling articulation of the shaft about the articulating section, to a second state for disabling articulation of the shaft about the articulating section. A control system is configured to control transitioning of the conductive leads between the first and second states.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
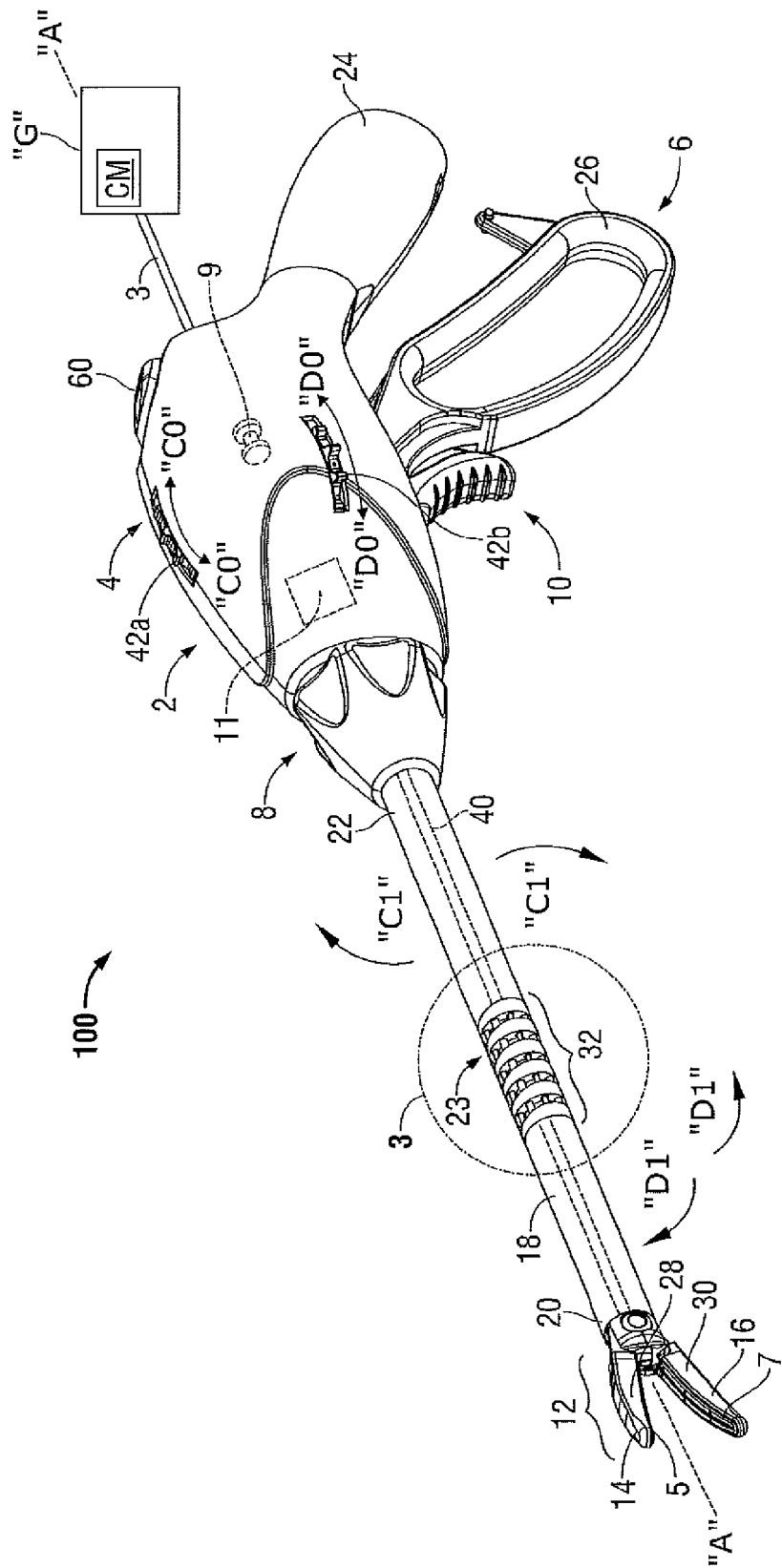
FIG. 1 is a side, perspective view of a system including an endoscopic instrument for performing an electrosurgical procedure according to an embodiment of the present disclosure.

With reference to FIGS. 1-4, and with initial reference to FIG. 1, an illustrative embodiment of a system 100 for performing an electrosurgical procedure is shown including an electrosurgical generator G including one or more control modules CM, and an articulating surgical instrument, e.g., an articulating endoscopic instrument 2, such as, for example, an articulating endoscopic forceps 2 (forceps 2), that is adapted to operatively and selectively couple to the electrosurgical generator G. As can be appreciated, other types of articulating instruments that are configured to treat tissue may be utilized in accordance with the present disclosure, e.g., snares, blades, loops, endoscopes, stabilizers, retractors, etc.

Continuing with reference to FIG. 1, electrosurgical generator G (generator G) is configured for performing an electrosurgical procedure. An electrosurgical procedure may include sealing, cutting, cauterizing, coagulating, desiccating, and fulgurating tissue all of which may employ RF energy. The generator G may be configured for monopolar and/or bipolar modes of operation. The generator G may include or be in operative communication with one or more processors (not shown) in operative communication with the one or more control modules CM that are executable on one or more processors. The control module CM may be configured to instruct one or more modules to transmit electrosurgical energy, which may be in the form of a wave or signal/pulse, via one or more cables (e.g., an electrosurgical cable 3) to one or both seal plates 5, 7 disposed on respective jaw housings 28 and 30. However, in certain embodiments, the forceps 2 may be battery powered. Moreover, and in certain embodiments, the control module may be in operable communication with an articulation control system 11 ("ACS 11 that is in operable communication with the forceps 2, see FIGS. 1 and 2).

Figure 2:
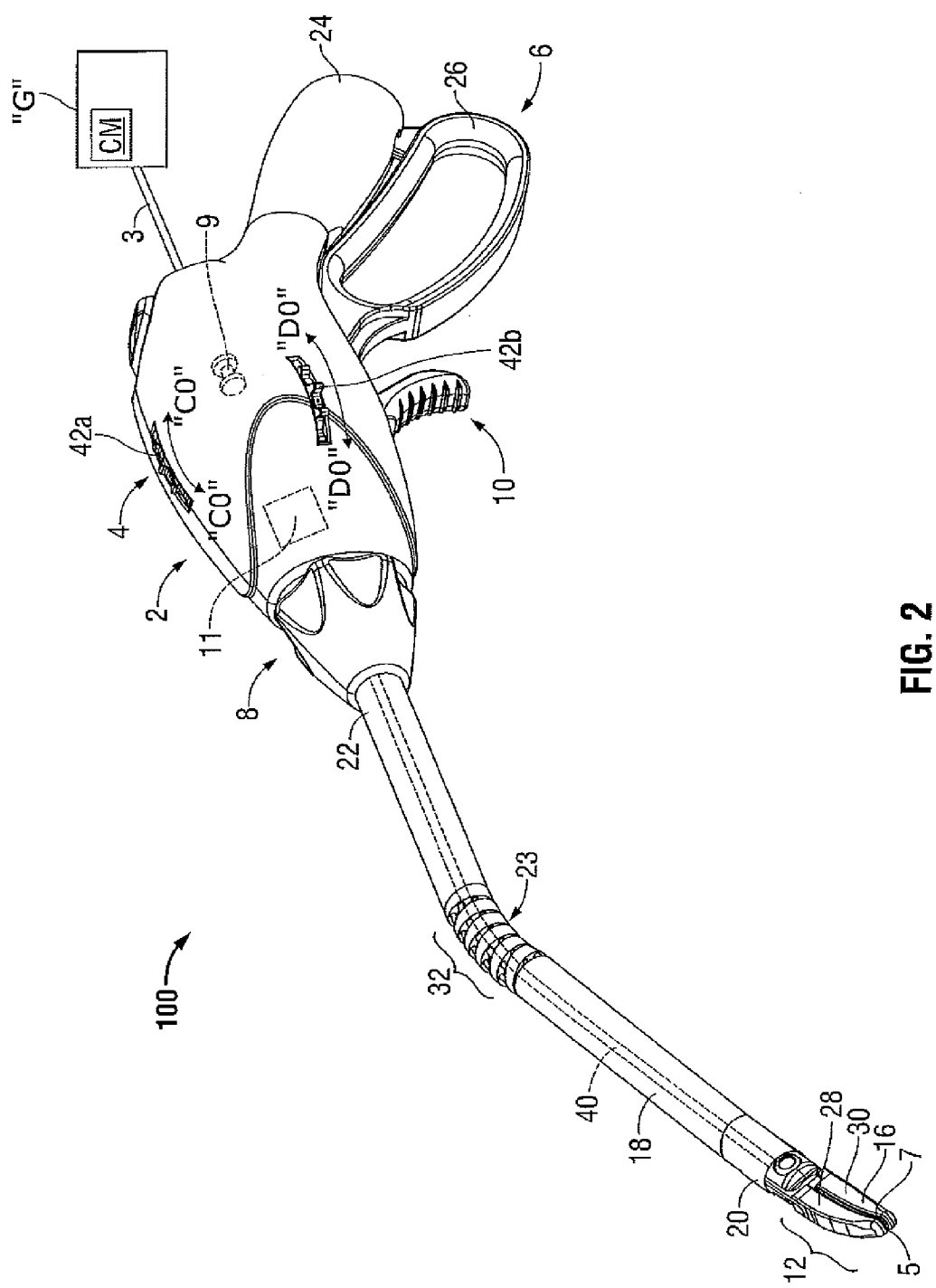
FIG. 2 is a side, perspective view of the endoscopic instrument depicted in FIG. 1 shown in an articulated configuration.

Continuing with reference to FIGS. 1 and 2, forceps 2 is shown configured for use with various electrosurgical procedures and generally includes a housing 4, an electrosurgical cable 3 that connects the forceps 2 to the generator G, a handle assembly 6, a rotating assembly 8, a trigger assembly 10, a drive assembly 9, and an end effector assembly 12 that operatively connects to the drive assembly 9. The drive assembly 9 may be in operative communication with handle assembly 6 for imparting movement of one or both of a pair of jaw members 14, 16 of end effector assembly 12.

For a more detailed description of the forceps 2 including rotating assembly 8, trigger assembly 10, and electrosurgical cable 3 (including line-feed configurations and/or connections), reference is made to commonly owned U.S. Pat. Publication No. 2007/0173814 filed on Nov. 9, 2006.

With continued reference to FIGS. 1 and 2, housing 4 is illustrated. Housing 4 is accessible by a surgeon from outside a body cavity to control the positioning, orientation and operation of the end effector 12 when the end effector 12 is positioned inside a body cavity at a surgical site. To provide this operability, the housing 4 supports various components that are operable to induce or prohibit movement in the end effector 12 through various modes. More particularly housing 4 is configured to house or support handle assembly 6, drive assembly 9, ACS 11 and a pair of articulation dials 42a, 42b.

Articulation dials 42a, 42b are operable to pivot the distal end 20 of an elongated shaft 18 to various articulated orientations with respect to the longitudinal axis A-A (FIGS. 1 and 2). More particularly, articulation dials 42a and 42b operably couple to a plurality of cables or tendons 34 that are in operative communication with an articulating section 23 of the shaft 18, as described in greater detail below. Articulation dial 42a may be rotated in the direction of arrows "C0" to induce pivotal movement in a first plane, e.g., a vertical plane, as indicated by arrows "C1", see FIG. 1. Similarly, articulation dial 42b may be rotated in the direction of arrows "D0" to induce pivotal movement in a second plane, e.g., a horizontal plane, as indicated by arrows "D1", see FIG. 1. Rotation of the articulation dials 42a and 42b in either direction of arrows "C0" or "D0" results in the tendons 34 pivoting or articulating the shaft 18 about the articulating section 23.

Shaft 18 includes a generally elongated configuration and defines a longitudinal axis "A-A" therethrough (FIG. 1). Shaft 18 has a distal end 20 configured to mechanically engage the end effector assembly 12 and a proximal end 22 that mechanically engages the housing 4, FIGS. 1 and 2. In the drawings and in the descriptions that follow, the term "proximal," as is traditional, will refer to the end of the forceps 2 that is closer to the user, while the term "distal" will refer to the end of the forceps 2 that is farther from the user.

Figure 3:
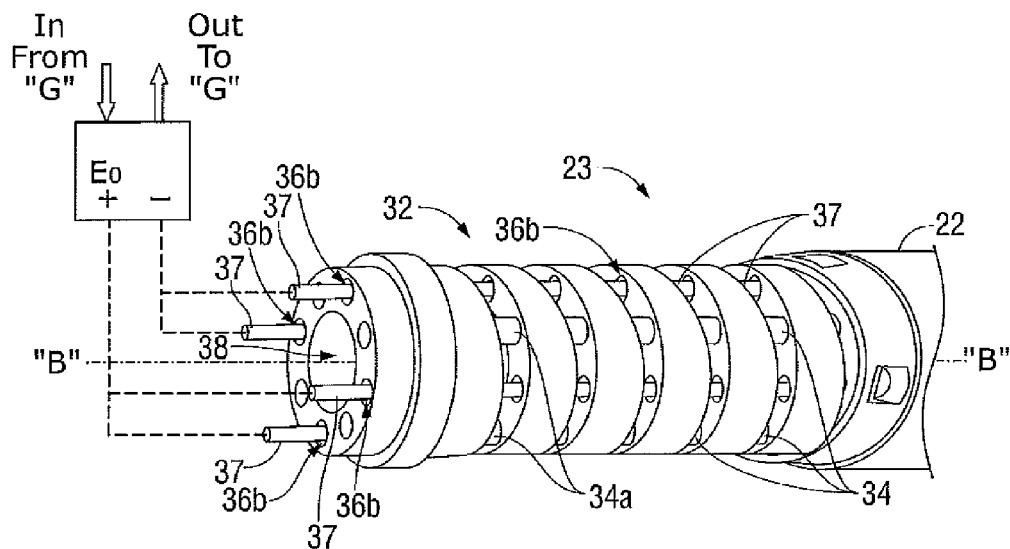
FIG. 3 is an enlarged area of detail depicted in FIG. 1 including electrical connections.
Figure 4:
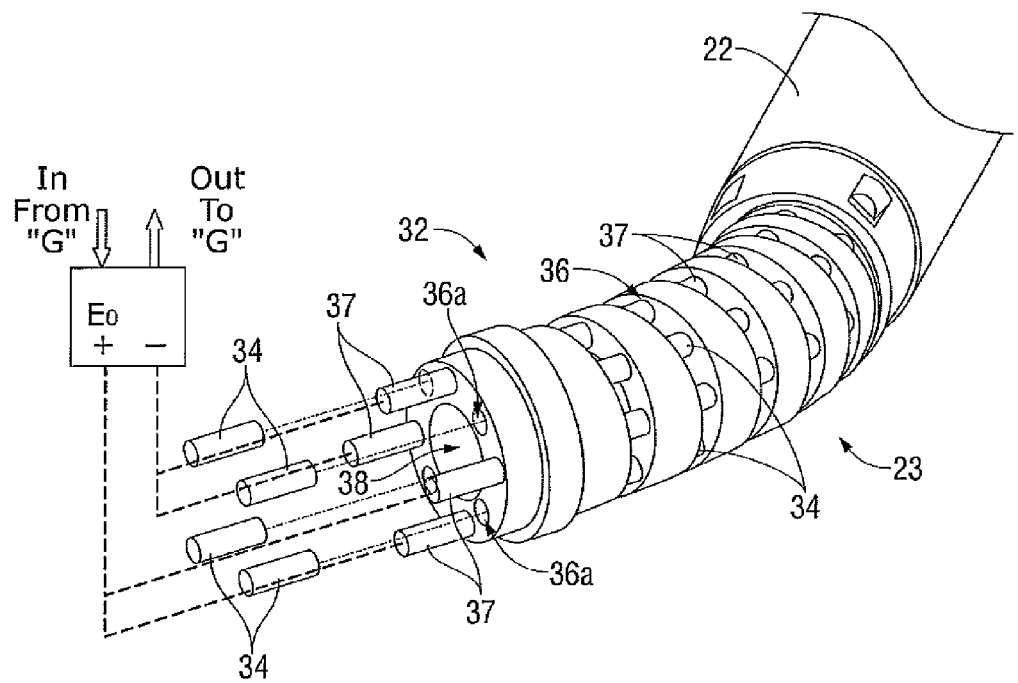
FIG. 4 is an enlarged area of detail depicted in FIG. 2 including electrical connections.

With reference to FIGS. 1-4, the articulating portion or section 23 is operably disposed on or coupled to the shaft 18 between the proximal and distal ends 22 and 20, respectively. In the embodiment illustrated in FIGS. 1-4, the articulation section 23 is defined by a plurality of articulating links 32 (links 32), as best seen in FIGS. 3-4. The links 32 are configured to articulate the shaft 18 transversely across the longitudinal axis "A-A" in either a horizontal or vertical plane, see FIGS. 2 and 4. For illustrative purposes, the shaft 18 is shown articulated across the horizontal plane.

The links 32 collectively define a central annulus 38 (FIGS. 3 and 4) therethrough that is configured to receive a drive mechanism, e.g., a drive rod 40 (FIGS. 1 and 2), therethrough. As can be appreciated, the configuration of the central annulus 38 provides adequate clearance for the drive rod 40 therethrough. The central annulus 38 defines an axis "B-B" therethrough that is parallel to the longitudinal axis "A-A" when the shaft 18 is in a non-articulated configuration, see FIG. 3.

Continuing with reference to FIGS. 3-4, the links 32 are operably coupled to articulation dials 42a and 42b via tendons 34. For illustrative purposes, four (4) tendons 34 are shown. The tendons 34 may be constructed of stainless steel wire or other material suitable for transmitting tensile forces to a distal-most link of links 32. Regardless of the construction materials, the tendons 34 exhibit a spring rate that is amplified over the length of the tendons 34 and thus, the tendons 34 may tend to stretch when external loads are applied to the elongated shaft 18. This tendency to stretch may be associated with an unintended change in orientation of the distal portion 22 of the elongated shaft 18, e.g., without a corresponding movement of the articulation dials 42a, 42b initiated by the surgeon.

The tendons 34 operably couple to the articulating dials 42a and 42b that are configured to actuate the tendons 34, i.e., "pull" the tendons 34, when the articulating dials 42a and 42b are rotated. The plurality of tendons 34 operably couple to the links 32 via one or more suitable coupling methods. More particularly, each link of the links 32 includes a corresponding plurality of first apertures or bores 36a defined therein (four (4) bores 36a are shown in the representative figures) that are radially disposed along each link of the links 32 and centrally aligned along a common axis, see FIG. 3. Each bore of the plurality of bores 36a is configured to receive a corresponding tendon 34. A distal end of each tendon 34 is operably coupled to a distal most link of the links 32 by suitable methods, e.g., one or more of the coupling methods described above.

Continuing with reference to FIGS. 3-4, each link 32 includes a second plurality of bores 36b (four (4) bores 36b are shown in the representative drawings, as best seen in FIG. 3). Each bore 36b is configured to receive a corresponding conductive lead of a plurality of conductive leads 37 (four (4) conductive leads 37 are shown in the representative drawings). The conductive leads 37 are configured to transition between first and second states within the second plurality of bores 36b. To facilitate transitioning of the conductive leads 37, each of the bores 36b includes a diameter that is greater than a diameter of each of the conductive leads 37 when the conductive leads 37 are in the first state.

The first and second bores 36a and 36b are disposed parallel with respect to the axis "B-B" of the central annulus (FIGS. 3 and 4). Moreover, the first and second bores 36a and 36b are equally spaced-apart from each other along a radial circumference of each of the links 32 (FIGS. 3 and 4).

With reference again to FIGS. 3-4, the conductive leads 37 are illustrated. The conductive leads 37 are configured to control articulation of the articulating section 21 of the shaft 18. With this purpose in mind, and as noted above, the conductive leads 37 are configured to transition between first and second states. More particularly, the conductive leads 37 transition from a first state, wherein the conductive leads 37 are free to move along the axis defined through each bore 36b (see FIG. 3, for example), to the second state, wherein the conductive leads 37 are fixed from translation, i.e., are stationary, along the axis defined through each bore 36b, see FIG. 4, for example. In the second state, an interference fit is formed between the conductive leads 37 and second plurality of bores 36b. That is, in the second state, the conductive leads 37 are configured to function as beam elements (i.e., the conductive leads 37 resist bending) that prevent articulation of the shaft 18 about the articulation section 23. As can be appreciated, a varying resistance to bending can be controlled and applied at any time during and/or after articulation movement to suit the needs of an end user by control of an expansion force and resulting friction between the second plurality of bores 36b and the conductive leads 37 disposed therein.

In accordance with the present disclosure, the conductive leads 37 are positioned through the second plurality of bores 36b to provide electrical continuity between the conductive leads 37 and the ACS 11 (FIGS. 3 and 4). As illustrated in FIGS. 3 and 4, two leads of the conductive leads 37 are configured as input leads and two leads of the conductive leads 37 are configured as return leads. More particularly, each conductive lead of the conductive leads 37 is coupled to one another via a series or parallel configuration to form an electrical circuit with the ACS. In this way, articulation locking of the shaft 18 can be controlled by an on/off application of the electrical circuit.

To prevent shorting between the conductive leads 37 and each link of the links 32, an insulative substrate (not explicitly shown) encases each conductive lead 37. Alternatively, each 32 may be made from a non-conductive material to prevent shorting between the conductive leads 37 and links 32. The exact method of insulating each conductive lead 37 from each link 32 may be varied for a specific type of surgical instrument, a specific manufacturer's preference, etc.

In the illustrative embodiment, the plurality of conductive leads 37 is made from one or more suitable types of thermally expanding material. The thermally expanding material is configured such that with an induction of a voltage and current flow therethrough, a thermally induced expansion of the thermally expanding material occurs transitioning each lead 37 from the first state to the second state. Suitable thermally expanding materials may include copper, copper alloys, electrically conductive plastic materials and shape memory alloys, e.g., NITINOL. In the embodiment illustrated in FIGS. 1-4, each conductive lead 37 is made from a copper alloy that is relatively elastic in the first state and substantially or semi rigid in the second state.

With reference again to FIGS. 1-4, ACS 11 and the operative components associated therewith are supported within or on the housing 4. A switch 60 in the form of a handswitch or footswitch is operable to actuate the ACS 11. In the illustrated embodiment, a push-button switch 60 is operably supported on the housing 4 and is accessible to a user.

ACS 11 is in operable communication with the generator G and/or the control module CM via the electrosurgical cable 3 to provide power to the ACS 11. More particularly, ACS 11 includes electrical circuitry that is configured to selectively induce a voltage and current flow to the plurality of conductive leads 37 such that each conductive lead 37 transitions from the first state to the second state. To this end, the generator G provides a voltage potential Eo, e.g., five (5) volts, of suitable proportion to the ACS. The ACS, in turn, induces a voltage in each conductive lead of the conductive leads 37 and current flow therethrough. The current flow through each conductive lead 37 causes each conductive lead 37 to transition from the first state (FIG. 3) to the second state (FIG. 4). In the second state, the conductive lead 37 provides an interference fit between each conductive lead 37 and the corresponding bores 36b, as best seen in FIG. 4.

With reference again to FIGS. 1 and 2, handle assembly 6 includes a fixed handle 24 and a movable handle 26. Fixed handle 24 is integrally associated with housing 4 and movable handle 26 is movable relative to fixed handle 24. Movable handle 26 of handle assembly 6 is ultimately connected to the drive assembly 9, which together mechanically cooperate to impart movement of one or both of the jaw members 14 and 16 to move from an open position (FIG. 1), wherein the jaw members 14 and 16 are disposed in spaced relation relative to one another, to a clamping or closed position, wherein the jaw members 14 and 16 cooperate to grasp tissue therebetween (FIG. 2).

Drive assembly 9 (FIGS. 1 and 2) including the drive rod 40 is in mechanical communication with the movable handle 26. More particularly, one or more gears, links, springs, or other component(s) that are operably supported and/or disposed within the housing 4 are configured to collectively provide translation of the drive rod 40 along the longitudinal axis "A-A" as a result of proximal movement of the movable handle 26. Drive rod 40 may be made from any suitable material, e.g., metal. In certain embodiments, it may prove advantageous for the drive rod 40 to be relatively flexible. In this instance, the drive rod 40 may be made from a relatively flexible material, e.g., wire, band, cable, etc.

Jaw members 14, 16 are operatively and pivotably coupled to each other and located adjacent the distal end 20 of shaft 18 (FIGS. 1 and 2). For illustrative purposes, the end effector 12 is shown including a bilateral jaw configuration, i.e., both jaw members 14 and 16 are movable. However, the present disclosure contemplates that the end effector 12 may include a unilateral jaw configuration, i.e., jaw member 14 is movable with respect to jaw member 16 that is non-movable or stationary with respect to jaw member 14. Respective electrically conductive seal plates 5 and 7 are operably supported on and secured to jaw housings 28 and 30 of respective the jaw members 14 and 16.

In use, jaw members 14 and 16, initially, are in open position (FIG. 1) and the plurality of conductive leads 37 are in the first state (FIG. 3). To position the jaw members 14 and 16 adjacent target tissue, one or both of the articulation dials 42a and 42b may be rotated to articulate the shaft 18 about articulating section 23 and transversely across the longitudinal axis "A-A." With the jaw members 14 and 16 in a position that is satisfactory to a user, push-button 60 pressed, which, in turn, actuates the ACS 11 to induce a voltage and current flow through the conductive leads 37. The conductive leads 37, being made from the thermally expanding material, expand, thus, forming an interference fit between the conductive leads 37 and the second plurality of bores 36b (FIG. 4). When the conductive leads 37 are in the second state (FIGS. 2 and 4) the tendons 34 is "unloaded" and not under high tension as is typically the case with conventional shafts that are configured to articulate. As can be appreciated, the tendons 34 retain their ability to stretch and the stiffness of the shaft 18 is not compromised.

From the foregoing and with reference to the various figure drawings, those skilled in the art will appreciate that certain modifications can also be made to the present disclosure without departing from the scope of the same. For example, in certain instances, to simplify manufacture of the shaft 18, it may prove advantageous to have a shaft with an articulating portion that includes a compliant cylindrical extrusion. In this instance, the entire shaft 18 may be made from a compliant extrusion. An interior of the shaft 18 may include apertures or lumens that are formed during the extrusion process of the shaft 18. The lumens take the place of the first and second plurality of bores 36a and 3b. To this end, the lumens may extend along a length of the shaft 18 such that a desired amount of articulation may be achieved.

It is contemplated that in some embodiments, it may prove advantageous to utilize the use of pneumatics or hydraulics to achieve the desired expansion characteristics within the second plurality of bores 36b. As can be appreciated, in the this instance the ACS 11 will be configured to provide one or more suitable types of fluids to a plurality of fluid lines that extend through the second plurality of bores 36b. In the instance, the fluid lines function similar to that of the conductive leads 37.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An endoscopic instrument, comprising:
    a housing having shaft extending therefrom that defines a longitudinal axis therethrough, the shaft including an articulating section disposed thereon, the articulating section including a plurality of links aligned along a length of the articulating section, each link of the plurality of links defines an annulus and first and second pluralities of bores, the plurality of links configured such that the annulus of the articulating section is collectively defined by the individual annuluses of each link of the plurality of links and the first and second pluralities of bores are collectively defined by the first and second pluralities of bores on each link of the plurality of links, the first plurality of bores configured to receive corresponding tendons therethrough and the second plurality of bores configured to receive a corresponding conductive leads therethrough; and
    an end effector assembly operatively connected to a distal end of the shaft configured for treating tissue includes a pair of first and second jaw members,
    wherein the corresponding conductive leads transition from a first state for enabling articulation of the shaft about the articulating section, to a second state for disabling articulation of the shaft about the articulating section.

2. An endoscopic instrument according to claim 1, wherein the first and second pluralities of bores are disposed parallel with respect to an axis that is parallel to the longitudinal axis defined through the shaft and defined through the central annulus.

3. An endoscopic instrument according to claim 2, wherein the first and second pluralities of bores are equally spaced-apart from each other along a radial circumference of each of the corresponding plurality of links.

4. An endoscopic instrument according to claim 1, further comprising an articulation control system that is in operative communication with the endoscopic instrument, the articulation control system configured to control transitioning of the conductive leads between the first and second states.

5. An endoscopic instrument according to claim 4, wherein the conductive leads are positioned through the second plurality of bores to provide electrical continuity between the conductive leads and the articulation control system.

6. An endoscopic instrument according to claim 1, wherein the conductive leads are made from a thermally expanding material.

7. An endoscopic instrument according to claim 6, wherein an insulative substrate encases the conductive leads to prevent shorting between the conductive leads and the plurality of links.

8. An endoscopic instrument according to claim 7, wherein each link of the plurality of links is made from a non-conductive material to prevent shorting between the conductive leads and the plurality of links.

9. An endoscopic instrument according to claim 7, wherein the thermally expanding material is configured such that an induction of a voltage and current induces thermal expansion of the thermally expanding material to transition the conductive leads from the first state to the second state.

10. An endoscopic instrument according to claim 7, wherein the thermally expanding material is selected from the group consisting of copper, copper alloys, electrically conductive plastic materials and shape memory alloys.

11. An endoscopic instrument according to claim 1, wherein a diameter of the conductive leads is less than a diameter of the second plurality of bores such that in the first state the conductive leads are freely moveable within the second plurality of bores and in the second state the conductive leads produce an interference fit between the conductive leads and the second plurality of bores.

12. An endoscopic instrument according to claim 1, wherein in the second state the conductive leads are capable of maintaining the articulating section in one of an articulated and non-articulated configuration.

13. A system for performing an electrosurgical procedure, comprising:
- an electrosurgical generator configured to transmit one or more suitable frequencies of electro surgical energy;
- an endoscopic instrument, comprising:
  - a housing having shaft extending therefrom that defines a longitudinal axis therethrough, the shaft including an articulating section disposed thereon, the articulating section having a central annulus extending therealong and first and second pluralities of bores, the first plurality of bores configured to receive corresponding tendons therethrough and the second plurality of bores configured to receive corresponding conductive leads therethrough;
  - an end effector assembly operatively connected to a distal end of the shaft configured for treating tissue includes a pair of first and second jaw members,
  - wherein the corresponding conductive leads transition from a first state for enabling articulation of the shaft about the articulating section, to a second state for disabling articulation of the shaft about the articulating section, wherein the conductive leads are made from a thermally expanding material made from a metal selected from the group consisting of copper, copper alloys, electrically conductive plastic materials and shape memory alloys, the thermally expanding material configured such that an induction of a voltage and current induces thermal expansion of the thermally expanding material to transition the conductive leads from the first state to the second state; and
  - a control system that is in operative communication with the endoscopic instrument, the control system configured to control transitioning of the conductive leads between the first and second states.

14. A system according to claim 13, wherein a diameter of the conductive leads is less than a diameter of the second plurality of bores such that in the first state the conductive leads are freely moveable within the second plurality of bores and in the second state the conductive leads produce an interference fit between the conductive leads and the second plurality of bores, wherein in the second state the conductive leads are capable of maintaining the articulating section in one of an articulated and non-articulated configuration.

15. An endoscopic instrument, comprising:
- a housing having shaft extending therefrom that defines a longitudinal axis therethrough, the shaft including an articulating section disposed thereon, the articulating section is further defined by a plurality of links aligned along a length of the articulating section, the articulating section having a central annulus extending therealong and first and second pluralities of bores, wherein the first and second pluralities of bores are disposed parallel with respect to an axis that is parallel to the longitudinal axis defined through the shaft and defined through the central annulus, the first plurality of bores configured to receive corresponding tendons therethrough and the second plurality of bores configured to receive a corresponding conductive leads therethrough; and
- an end effector assembly operatively connected to a distal end of the shaft configured for treating tissue includes a pair of first and second jaw members,
- wherein the corresponding conductive leads transition from a first state for enabling articulation of the shaft about the articulating section, to a second state for disabling articulation of the shaft about the articulating section.

16. An endoscopic instrument according to claim 15, wherein the first and second pluralities of bores are equally spaced-apart from each other along a radial circumference of each of the corresponding plurality of links.

17. An endoscopic instrument, comprising:
- a housing having shaft extending therefrom that defines a longitudinal axis therethrough, the shaft including an articulating section disposed thereon, the articulating section having a central annulus extending therealong and first and second pluralities of bores, the first plurality of bores configured to receive corresponding tendons therethrough and the second plurality of bores configured to receive corresponding conductive leads therethrough, the conductive leads made from a thermally expanding material;
- an insulative substrate configured to encase the conductive leads to prevent shorting between the conductive leads and the plurality of links; and
- an end effector assembly operatively connected to a distal end of the shaft configured for treating tissue includes a pair of first and second jaw members,
- wherein the corresponding conductive leads transition from a first state for enabling articulation of the shaft about the articulating section, to a second state for disabling articulation of the shaft about the articulating section, and
- wherein the thermally expanding material is configured such that an induction of a voltage and current induces thermal expansion of the thermally expanding material to transition the conductive leads from the first state to the second state.

* * * * *